United States Patent
Wong et al.

(10) Patent No.: US 9,474,736 B2
(45) Date of Patent: **\*Oct. 25, 2016**

(54) COMPOSITION AND METHOD FOR TREATING DRY EYE SYNDROME

(71) Applicant: RAMSCOR, INC., Menlo Park, CA (US)

(72) Inventors: Vernon G. Wong, Menlo Park, CA (US); Louis L. Wood, Potomac, MD (US)

(73) Assignee: Ramscor, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/835,489

(22) Filed: Aug. 25, 2015

(65) Prior Publication Data

US 2015/0359779 A1 Dec. 17, 2015

Related U.S. Application Data

(63) Continuation of application No. 14/218,125, filed on Mar. 18, 2014, now Pat. No. 9,144,566, which is a continuation of application No. 12/576,834, filed on Oct. 9, 2009, now Pat. No. 8,722,728.

(60) Provisional application No. 61/104,110, filed on Oct. 9, 2008.

(51) Int. Cl.
*A61K 31/355* (2006.01)
*A61K 9/00* (2006.01)
*A61K 31/35* (2006.01)

(52) U.S. Cl.
CPC ........... *A61K 31/355* (2013.01); *A61K 9/0048* (2013.01); *A61K 31/35* (2013.01)

(58) Field of Classification Search
CPC ........................ A61K 31/35; A61K 31/355
See application file for complete search history.

(56) References Cited

U.S. PATENT DOCUMENTS

| | | |
|---|---|---|
| 5,886,030 A | 3/1999 | Maniar |
| 6,555,575 B2 | 4/2003 | Wechter |
| 6,716,451 B1 | 4/2004 | Udell et al. |
| 6,733,786 B1 | 5/2004 | Kim et al. |
| 8,722,728 B2 | 5/2014 | Wong et al. |
| 2004/0029954 A1 | 2/2004 | Wechter |
| 2004/0082649 A1 | 4/2004 | Rich et al. |
| 2006/0073182 A1 | 4/2006 | Wong et al. |
| 2006/0241174 A1 | 10/2006 | Mueller et al. |
| 2008/0015250 A1 | 1/2008 | Friedlaender et al. |
| 2008/0038316 A1 | 2/2008 | Wong et al. |
| 2009/0092665 A1 | 4/2009 | Mitra et al. |
| 2009/0136445 A1 | 5/2009 | Wong et al. |

FOREIGN PATENT DOCUMENTS

| | | |
|---|---|---|
| CN | 1129400 A1 | 8/1996 |
| WO | 00/02554 A1 | 1/2000 |

OTHER PUBLICATIONS

Nagata et al., J. Ocul. Pharmacol. Ther., 15(4):345-350 (1999).
Kojima et al., Inves. Ophthalmol. Visual Sci., 43:116-120 (2002).
International Search Report mailed, Apr. 29, 2010, cited in related International Application No. PCT/US2009/060200, filed Oct. 9, 2009.
International Preliminary Report on Patentability and Written Opinion mailed, Apr. 21, 2011, cited in related International Application No. PCT/US2009/060200, filed Oct. 9, 2009.
Office Action issued, on Sep. 13, 2012, in related Chinese Application No. 200980140567.6, filed Oct. 9, 2009.
Extended European Search Report mailed, Nov. 16, 2012, cited in related European Application No. 09819968.0, filed Oct. 9, 2009.

*Primary Examiner* — Zohreh Fay

(74) *Attorney, Agent, or Firm* — Wiley Rein LLP

(57) ABSTRACT

The present invention provides for compositions, medicaments, and methods for treating or alleviating the symptoms of dry eye syndrome or chronic dry eye. More specifically, the present embodiments provide for medicaments consisting of tocopherol or tocotrienol eyedrops. A single topical administration of tocopherol or tocotrienol eyedrops in the eyes of a subject suffering from dry eye alleviates symptoms for at least one day. In particular, the eyedrop medicament consists of α-tocopheryl acetate; α-tocopheryl acetate and about 0.5% aqueous component; or α-tocopheryl acetate, about 2.5% tocopherol emulsifier, and about 20% to about 30% aqueous excipient.

26 Claims, 3 Drawing Sheets

COMPOSITION AND METHOD FOR TREATING DRY EYE SYNDROME

RELATED APPLICATIONS

This application is a continuation of U.S. patent application Ser. No. 14/218,125, filed Mar. 14, 2014, which is a continuation of Ser. No. 12/576,834, filed Oct. 9, 2009, now U.S. Pat. No. 8,722,728, issued on May 13, 2014, which claims the priority benefit of U.S. Patent Application Ser. No. 61/104,110, filed Oct. 9, 2008, all of which are incorporated herein by reference.

FIELD OF THE INVENTION

The present invention relates to compounds and methods for alleviating symptoms of dry eye syndrome. In particular, the invention relates to vitamin E eyedrops which provide sustained relief from dry eye symptoms.

BACKGROUND

Dry eye syndrome, or chronic dry eye (CDE) is a chronic lack of sufficient lubrication and moisture in the eye. Its consequences range from subtle but constant irritation to ocular inflammation of the anterior (front) tissues of the eye. The symptoms include persistent dryness, scratching, redness, and burning in the eyes, and some people also experience a foreign body sensation: the feeling that something is in the eye. In CDE, the eye either does not produce enough tears, or produces tears that evaporate too quickly. Sometimes, watery eyes can result from dry eye syndrome, because the excessive dryness over-stimulates production of the watery component of tears. Tears are composed of three layers: the outer, oily, lipid layer; the middle, watery, lacrimal layer; and the inner, mucous or mucin layer. Each layer is produced by a different part of the eye (the lacrimal gland produces the lacrimal layer, for example), so problems with any one of these sources can result in dry eyes.

CDE has several causes. It occurs as a part of the natural aging process, especially during menopause; as a side effect of many medications, such as antihistamines, antidepressants, certain blood pressure medicines, Parkinson's medications, and birth control pills; wearing contact lenses; smoking; or because of a dry, dusty or windy climate. Air conditioning or dry heating systems can also dry out the eyes. Another cause is insufficient blinking, which often occurs in occupations that require staring at computer screens. Incomplete closure of the eyelids, eyelid disease and a deficiency of the tear-producing glands are other causes. Dry eye complaints are occasionally associated with incomplete closure of eyelids following cosmetic eyelid surgery (blepharoplasty). Risk factors for CDE include hormonal changes (related to aging and menopause), medical conditions (e.g., diabetes), and autoimmune disease (e.g., Sjogren's Syndrome).

CDE is an ongoing condition that may not be cured (depending on the cause), but the accompanying dryness, scratchiness, and burning can be managed. Artificial tears, which are lubricating eyedrops, may alleviate the dry, scratching feeling. Restasis® eyedrops (0.05% cyclosporine in a castor oil base) also help eyes increase tear production. Restasis® eyedrops are placed in the affected eye(s) twice a day, about 12 hours apart. These eye drops must be mixed well before use, and the eye drops have a milky white appearance.

Many people attempt to treat their dry eyes with normal eyedrops rather than artificial tears, perhaps because normal eyedrops are significantly less expensive than artificial tears (typically only a fifth of the cost of generic cyclosporine-containing drops), and do not require a prescription. These drops can reduce or temporarily eliminate eye redness, but they do not treat the cause of the redness: whether it is dryness, environmental irritation, or some other problem. Additionally, the vasoconstrictors in common eyedrop formulas, that reduce redness by contracting the eye's blood vessels, lose their effectiveness over time such that more and more is needed to achieve the same effect.

Hence, there remains a need for inexpensive, effective, and long-term medicament for treating CDE.

SUMMARY OF THE INVENTION

The present invention provides for compounds, medicaments and methods for alleviating the symptoms or treating CDE (dry eye syndrome). The invention herein provides a safe, long-lasting, and relatively inexpensive alternative to existing CDE therapies.

An embodiment of the present invention provides for a medicament consisting of tocopherol or tocotrienol for use as an eyedrop for treating CDE. In a particular embodiment, the tocopherol is α-tocopheryl acetate.

Another embodiment of the present invention provides for a method of treating CDE comprising placing a drop of tocopherol or tocotrienol in the eye(s) of the subject suffering from CDE. In a particular embodiment, the tocopherol is α-tocopheryl acetate. In another aspect, this method provides relief from CDE symptoms for at least about one day, such as for about four days or about seven days.

Another embodiment provides for a medicament consisting of tocopherol or tocotrienol, also including small amounts (e.g., about 0.5%) of absorbed isotonic aqueous solutions for treating CDE. In a particular embodiment, the tocopherol or tocotrienol is mixed with the aqueous solution, such as saline, and formulated as a topical eyedrop.

An additional embodiment consists of tocopherol and a tocopherol emulsifier such as TPGS (α-tocopheryl succinate esterified to polyethylene glycol 1000[PEG 1000]). TPGS may be used in tocopherol formulations (such as dl-α tocopheryl acetate) to increase the aqueous component over about 0.5% (wt). For example, a stable mixture of aqueous and α-tocopheryl acetate (EA) may be prepared in ratios ranging from about 1:2 to 1:4 (aqueous:EA) with TPGS added at about 2.5% as an emulsifier. These emulsions are stable, and suitable as topical formulations including eyedrops.

DETAILED DESCRIPTION

Figure 1:
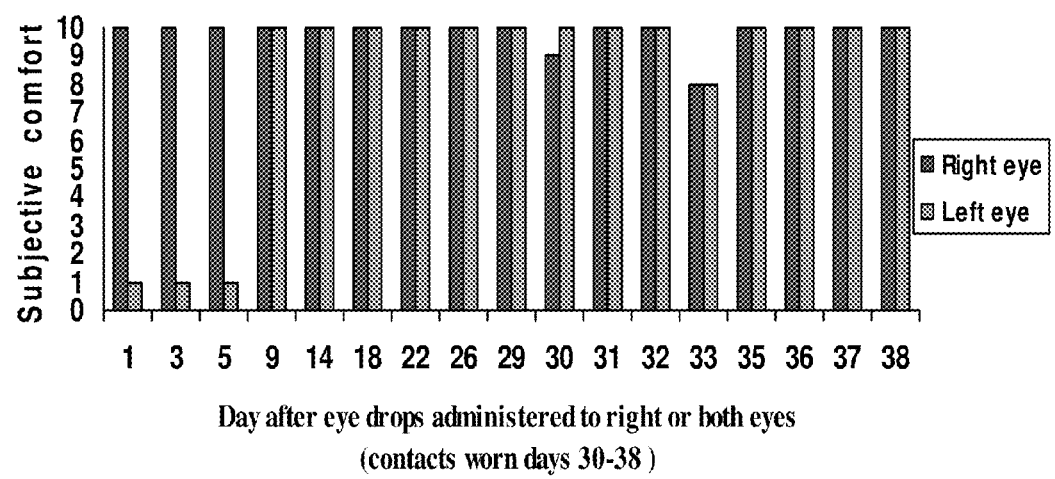
FIG. 1 is a bar graph depicting the subjective comfort of an individual applying a drop of α-tocopheryl acetate into the eye(s) before bedtime preceding the days indicated. Subjective comfort is depicted on a scale of 1 to 10; with 1 being very irritated, and right eye feeling swollen; and 10 being very comfortable and tolerable compared to no drops.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present embodiments provide for compositions and methods for treating CDE or dry eye syndrome. The invention herein provides a safe, long-lasting, and relatively inexpensive alternative to existing CDE therapies.

One embodiment of the present invention provides for a tocopherol or tocotrienol as the primary component of a topical medicament for the treatment of dry eye. In another embodiment, an eyedrop for treating CDE includes at least about 70% tocopherol or tocotrienol. For example, the eyedrop may include about 70% to about 100% tocopherol or tocotrienol, inclusive. Alternatively, the eyedrop may include about 99.5% tocopherol or tocotrienol. In another embodiment, the administration of an eyedrop of a tocopherol or tocotrienol, such as vitamin E, is placed in the eye(s) of the subject, and provides relief from symptoms for at least one day.

Tocopherols and tocotrienols are derivatives of the simplest tocopherol, 6-hydroxy-2-methyl-2-phytylchroman. Tocopherols are also known as a family of natural or synthetic compounds commonly called Vitamin E. $\alpha$-tocopherol is the most abundant and active form of this class of compounds. Other members of this class include $\beta$-, $\gamma$-, and $\delta$-tocopherols and $\alpha$-tocopherol derivatives such as $\alpha$-tocopheryl acetate. Useful tocotrienols include d-$\delta$-tocotrienols, and d-$\beta$-, d-$\gamma$-tocotrienols, and their esters. The tocopherols and tocotrienols of the present invention include the d, l, and dl isomers of the tocopherols, tocotrienols, and their esters. In particular, the tocopherols and their esters of low water solubility, notably $\alpha$-tocopheryl acetate, have been used as excipients in formulations for delivering pharmaceutical agents in topical eye drop formulations that provide sustained release of pharmaceutical agents for periods up to one week from a single application, without interfering with vision. Thus, the tocopherols of the present invention include $\alpha$-tocopherol, $\beta$-tocopherol, $\gamma$-tocopherol, $\delta$-tocopherol, tocopherol isomers and their esters, and tocopheryl isomer acetates such as $\alpha$-tocopheryl acetate. Tocopheryl esters useful in the present invention include tocopheryl and tocotrienyl esters with $C_1$ to $C_4$ straight and branched chain aliphatic carboxylic acids, such as dl-$\alpha$-tocopheryl acetate.

Tocopherols and tocotrienols may be produced by synthetic chemistry, or they may be obtained from natural sources such palm oils. In that regard, they may be obtained from bio-renewable and certified organic sources. Tocopherols and tocotrienols are available commercially, for example from, Sigma-Aldrich Corp. (St. Louis, Mo.), MP Biomedicals (Solon, Ohio), or Fuji Chemical Indus. (Nakaniikawa-gun, Toyama-Pref., Japan). Fully synthetic dl-tocopherol or dl-tocopheryl acetate are available from DSM (Heerlen, Netherlands) or BASF Corp. (Ludwigshafen am Rhein, Germany). Additionally, semisynthetic "natural source" vitamin E is available, made by converting common natural beta, gamma and delta tocopherol isomers into the alpha form by adding methyl groups to yield d-$\alpha$-tocopherol, from Archer Daniels Midland Co. (Decatur, Ill.), and Cargill, Inc. (Wayzata, Minn.).

Although tocopherols have been used as a component in eyedrop formulations for the delivery of other agents, or in combination with several other ingredients in formulations for treating CDE, the tocopherols have not been used in-and-of-themselves for the relief of CDE. Additionally, although vitamin E has been researched in the context of preventing chemical-induced cataracts (Nagata et al., 15(4) J. Ocul. Pharmacol. Ther. 345-50 (1999); Kojima et al., 43 Invest. Ophthalmol. Visual Sci. 43:1116-20 (2002)), there has been no commercial development of eye drops for the treatment of CDE in which the sole component of the medicament is vitamin E. Additionally, there has been no development of tocopherols for sustained treatment of CDE. More specifically, for example, the analyses of vitamin E and cataracts used treatments of 5-times-a-day, every day, for nine weeks. Nagata et al., 1999.

Moreover, the simplicity of the present eyedrop formulations eliminates side effects that may be caused by additional active agents and/or excipients. The present approach is also relatively inexpensive in terms of costs, quality control, and quality assurance.

The methods and compositions of the present invention provide for long-lasting alleviation of the symptoms of dry eye. For example, one drop of $\alpha$-tocopheryl acetate placed in each eye of one subject may provide relief for at least about one day, or for at least about four days. Relief from dry eye symptoms using the medicament of the present invention may last for one day, to one week, to several weeks, inclusive. For example, relief from dry eye symptoms using the medicament of the present invention may at least one day, at least several days, at least one week, at least two weeks, or at least three weeks.

Without being bound by theory, it is possible that once the eyedrop formulation of the instant invention is administered to the eye, the tocopherol therein absorbs water and other isotonic aqueous solutions found in tears, and thus acts as a reservoir that both absorbs and releases the aqueous component to the eye surface to alleviate dry eye symptoms. For example, tocopheryl acetate can absorb about 0.5% aqueous component and may act as a lubricating vehicle to distribute tears when needed. Thus, the aqueous component includes in vivo tears absorbed after placement in the eye and aqueous excipient components such as water or saline added to the tocopherol eyedrop formulation. In an embodiment of the invention, the eyedrop is 99.5% tocopherol or tocotrienol, such as α-tocopheryl acetate.

Additionally, the aqueous component of the tocopherol formulation may be increased to over about 0.5% with use of an additional tocopherol emulsifier such as TPGS (α-tocopheryl succinate esterified to polyethylene glycol 1000 [PEG 1000]), an FDA-approved lipophilic α-tocopherol. TPGS may be used in tocopherol formulations (such as dl-α tocopheryl acetate) to increase the aqueous component over about 0.5% (wt). For example, a stable mixture of saline and α-tocopheryl acetate (EA) may be prepared (for example, by sonication) in ratios ranging from about 1:2 to 1:4 (saline:EA) with TPGS added at about 2.5% as an emulsifier. Similarly, water and EA may be prepared in stable formulations at ratios ranging from about 1:2 to 1:4 ($H_2O$:EA), inclusive, with TPGS added at about 2.5% as an emulsifier. These formulations therefore comprise about 70% to about 80% EA. These emulsions are stable, and suitable as topical formulations including eyedrops.

EXAMPLES

Example 1. Topical Application of α-tocopheryl Acetate

One drop of α-tocopheryl acetate, about 50 μl in size, was applied as a drop in the right eye of one human volunteer, and in each of the eyes of another human volunteer, each of whom suffered from symptoms associated with dry eye syndrome and had active outdoor lifestyles. No irritation or blurred vision was reported. Both volunteers reported relief from dry eye symptoms for several days with no repeat applications of α-tocopheryl acetate during that time. Both subjects reported that relief from dry eye symptoms lasted for at least one day. One subject reported that the relief lasted at least seven days.

Example 2. Alleviation of CDE Symptoms in Contact Lenses-Wearing Individual

A 53-yr-old female volunteer used one drop of α-tocopheryl acetate in one or more eyes at night, and reported the irritation or comfort on a subjective scale of 1-to-10, (maximum irritation "1", maximum comfort "10") as shown in FIG. 1. At days 1 to 5, the individual placed one drop in the right eye only. The individual enjoyed comfort for up to five days before re-applying eyedrops. The individual was able to wear contact lenses (days 30-38) in relative comfort although she did not apply the eyedrops every single night.

Figure 2:
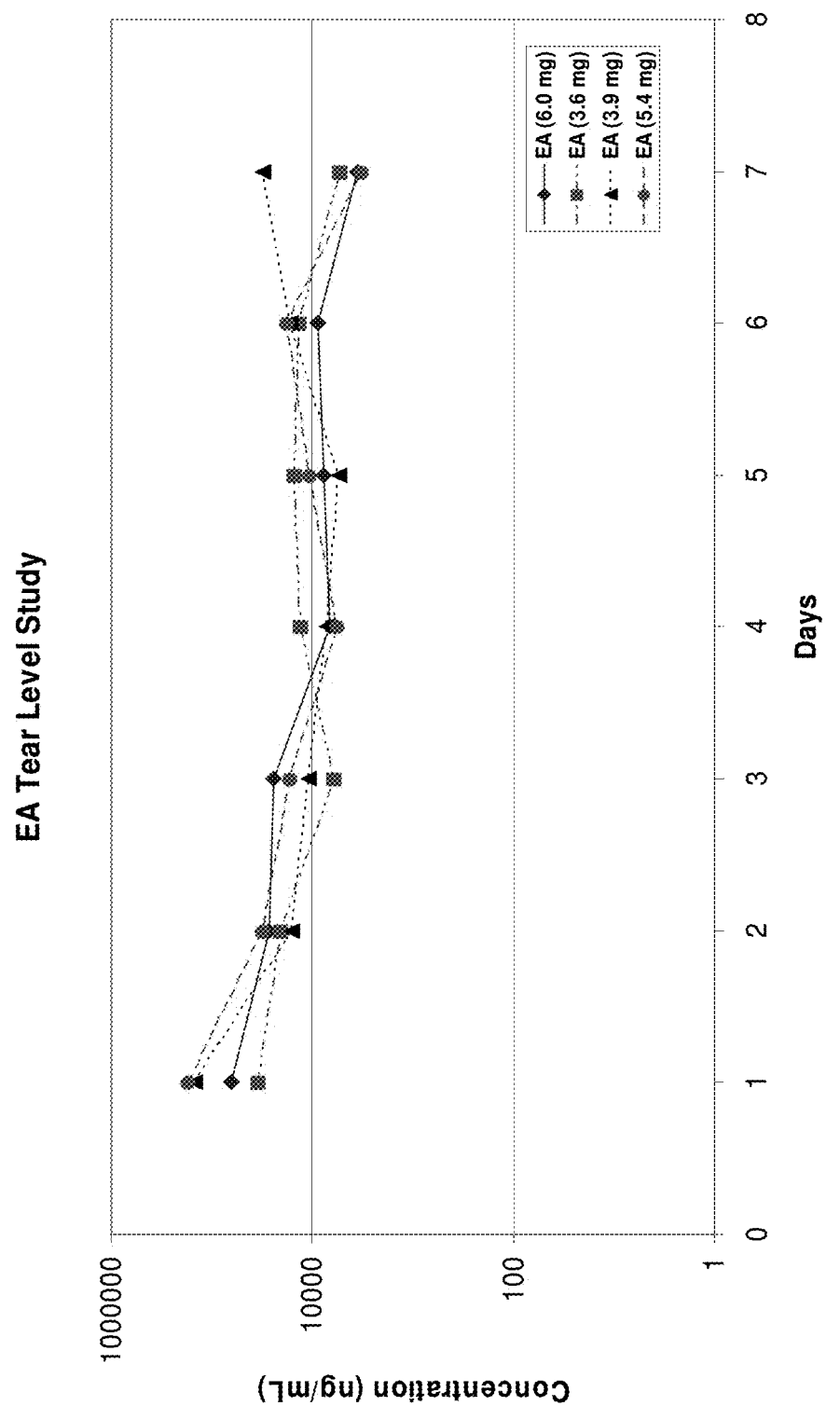
FIG. 2 is a graph showing the levels of α-tocopheryl acetate in the tears of rabbits over the course of seven days after the rabbits were administered one drop of α-tocopheryl acetate (3.6 mg, 3.9 mg, 5.4 mg, or 6.0 mg) on day one.

Example 3. Sustained Release of α-tocopheryl Acetate in the Tears of Rabbits Administered a Single Drop of α-tocopheryl Acetate Four adult New Zealand White (NZW) rabbits (two females, two males) each weighing 4.5 kilo to 5.0 kilo were used in this example. One drop of α-tocopheryl acetate, each weighing 3.6 mg, 3.9 mg, 5.4 mg and 6.0 mg, was instilled onto one eye of each animal. Tear samples were collected daily by filter paper, weighed, eluted in 300 μl MeOH and analyzed for tocopheryl acetate (EA) by LC/MS/MS. Detected tear levels of EA over a seven-day period ranged from 15 μg/ml to 36 μg/ml with a mean of 26 μg/ml (26,000 ng/ml). See FIG. 2. Detectable levels of EA in the cul-de-sac of the rabbit eye may last beyond seven days.

Example 4. Water Evaporation from Tocopherol/Water Emulsions

Figure 3:
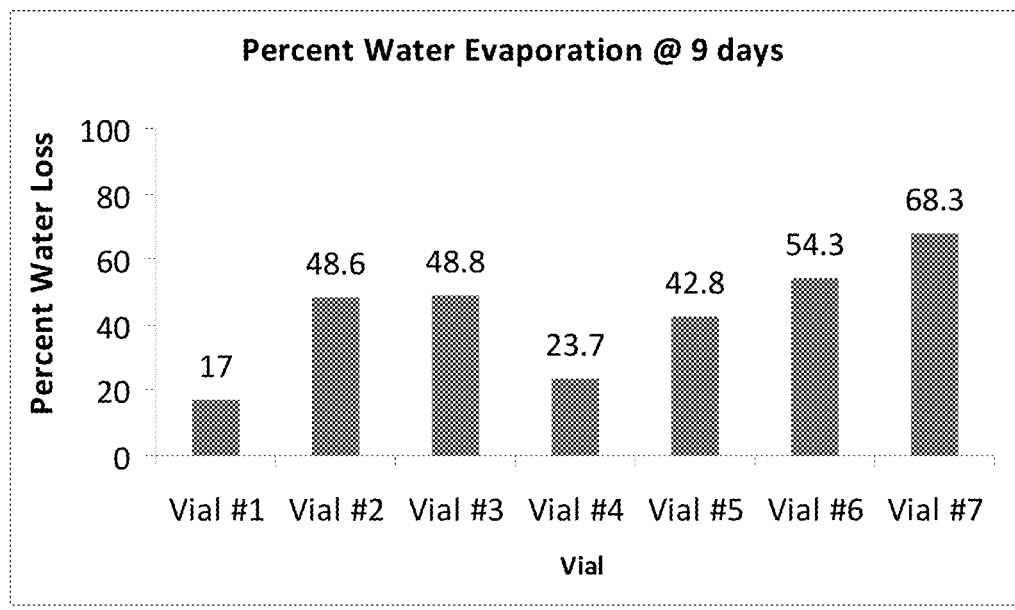
FIG. 3 is a bar graph depicting the percent water evaporation from a tocopherol/water emulsions at nine days, shown as the percent water lost.

Mixtures of α-tocopheryl acetate (EA), d-α-tocopheryl polyethylene glycol 1000 succinate (TPGS) and water were prepared at the ratios shown in Table 1, weighed, and placed in 20 ml-sized glass vials. Vials #1 through #6 were each capped and sonicated for two minutes to yield stable emulsions. The vials #1 through #8 were then uncapped and left at ambient conditions for nine days. All the emulsions in vials #1 through #6 remained stable. All vials were weighed subsequently to measure weight (water) loss. Vial #8, containing only EA, lost no weight, indicating that the weight losses in the other vials, that contained water, were due to water evaporation. Results are also depicted in FIG. 3.

TABLE 1

| Water evaporation from EA/water emulsions | | | | | | |
|---|---|---|---|---|---|---|
| vial # | water:EA | g water | g EA | g TPGS | g wt loss | % wt loss |
| 1 | 1:1 | 2.0960 | 2.0020 | 0.4035 | 0.3562 | 17.0 |
| 2 | 2:1 | 2.6824 | 1.3472 | 0.1026 | 1.3037 | 48.6 |
| 3 | 3:1 | 3.0240 | 1.0129 | 0.0997 | 1.4756 | 48.8 |
| 4 | 1:2 | 1.3300 | 2.6600 | 0.1011 | 0.3146 | 23.7 |
| 5 | 1:3 | 0.9988 | 2.9938 | 0.1023 | 0.4274 | 42.8 |
| 6 | 1:1 | 2.0163 | 2.0008 | 0.1024 | 1.095 | 54.3 |
| 7 | | 2.0330 | | | 1.388 | 68.3 |
| 8 | | | 1.9964 | | 0.0 | |

In an alternative study, the concentrations of water or saline that would remain stably absorbed in α-tocopheryl acetate (EA) were examined. Equal volumes of water or 0.9% saline were placed with EA in sealed vials at 30° C. Samples of the resultant EA plus absorbed aqueous were removed at several time points and the water contents were assayed by evaporative weight loss to constant weight over time at 30° C. open to the air. After 12 hrs exposure of EA to water or the saline solution in sealed vials at 30° C. the maximum amounts of aqueous solutions absorbed in EA were reached. The resultant values were: 0.3% water absorbed and 0.6% saline solution absorbed.

We claim:

1. A dosage form of an eyedrop medicament for the alleviation of dry eye symptoms, wherein said dosage form consists of a single eye drop of about 50 μL, wherein said medicament comprises at least about 70% of a tocopherol or tocotrienol and no additional active ingredient, wherein a single administration of a single dosage form of said eyedrop medicament alleviates the symptoms of dry eye for at least about four days.

2. The dosage form of claim 1, wherein said tocopherol or tocotrienol is selected from the group consisting of tocopheryl and tocotrienyl esters with $C_1$ to $C_4$ straight and branched chain aliphatic carboxylic acids, and d, l, dl isomers of tocopherols, tocotrienols and their esters.

3. The dosage form of claim 2, wherein said tocopheryl is a-tocopheryl acetate.

4. The dosage form of 1, wherein said medicament further comprises an aqueous component.

5. The dosage form of claim 4, wherein said aqueous component is about 0.5% of the said medicament.

6. The dosage form of claim 4, wherein said aqueous component is more than about 0.5% of the said medicament, and wherein said medicament further includes an emulsifier.

7. The dosage form of claim 6, wherein said emulsifier is d-α-tocopheryl polyethylene glycol 1000 succinate (TPGS).

8. The dosage form of claim 6, wherein the medicament prepared in ratios ranging from about 1:2 to 1:4 aqueous:tocopherol with emulsifier added at about 2.5%.

9. The use of the dosage form of eyedrop medicament of claim 1 for treating the symptoms of dry eye in a human.

10. A dosage form of an eyedrop medicament for the alleviation of dry eye symptoms consisting essentially of 50 µL of a tocopherol or tocotrienol, wherein a single administration of 50 µL of said eyedrop medicament alleviates the symptoms of dry eye for at least about four days.

11. The dosage form of claim 10, wherein said tocopherol or tocotrienol is selected from the group consisting of tocopheryl and tocotrienyl esters with $C_1$ to $C_4$ straight and branched chain aliphatic carboxylic acids, and d, l, dl isomers of tocopherols, tocotrienols and their esters.

12. The dosage form of claim 11, wherein said tocopheryl is α-tocopheryl acetate.

13. The dosage form of claim 10, wherein said medicament further consists of an aqueous component.

14. The dosage form of claim 13, wherein said aqueous component is about 0.5% of the said medicament.

15. The dosage form of claim 10, wherein said aqueous component is more than about 0.5% of the said medicament, and wherein said medicament further includes an emulsifier.

16. The dosage form of claim 15, wherein said emulsifier is d-α-tocopheryl polyethylene glycol 1000 succinate (TPGS).

17. The dosage form of claim 15, wherein said emulsifier is d-α-tocopheryl polyethylene glycol 1000 succinate (TPGS).

18. The use of the dosage form of claim 10 as a medicament for treating the symptoms of dry eye in a human.

19. A method of alleviating the symptoms of dry eye syndrome comprising topically administering about 50 µL of an eyedrop comprising at least about 70% tocopherol or tocotrienol with no additional active agents in the eye(s) of a subject suffering symptoms of dry eye on a twice-weekly basis, wherein a single administration of said eyedrop alleviates dry eye symptoms for at least about four days.

20. The method of claim 19, wherein said tocopherol or tocotrienol is α-tocopheryl acetate.

21. The method of claim 19, wherein said tocopherol or tocotrienol eyedrop further comprises about 0.5% aqueous component.

22. The method of claim 19, wherein said aqueous component is more than about 0.5% of the said medicament, and wherein said medicament further includes an emulsifier.

23. The method of claim 22, wherein said emulsifier is d-a-tocopheryl polyethylene glycol 1000 succinate (TPGS).

24. The method of claim 22, wherein the eyedrop is prepared in ratios ranging from about 1:2 to about 1:4 aqueous:tocopherol with emulsifier added at about 2.5%.

25. The dosage form of claim 2, wherein the medicament comprises about 99.5% tocopheryl acetate.

26. The method of claim 19, wherein the eyedrop comprises about 99.5% tocopheryl acetate.

* * * * *